United States Patent
Liu et al.

(10) Patent No.: US 10,274,564 B2
(45) Date of Patent: Apr. 30, 2019

(54) NON-INVASIVE TEMPERATURE MAPPING USING TEMPERATURE-RESPONSIVE WATER SATURATION SHIFT REFERENCING (T-WASSR) MRI

(71) Applicants: THE JOHNS HOPKINS UNIVERSITY, Baltimore, MD (US); KENNEDY KRIEGER INSTITUTE, INC., Baltimore, MD (US)

(72) Inventors: Guanshu Liu, Nottingham, MD (US); Assaf A. Gilad, Baltimore, MD (US); Michael T. McMahon, Columbia, MD (US); Peter C. Van Zijl, Ellicott City, MD (US)

(73) Assignees: THE JOHNS HOPKINS UNIVERSITY, Baltimore, MD (US); KENNEDY KRIEGER INSTITUTE, INC., Baltimore, MD (US)

( * ) Notice: Subject to any disclaimer, the term of this patent is extended or adjusted under 35 U.S.C. 154(b) by 892 days.

(21) Appl. No.: 14/428,713

(22) PCT Filed: Sep. 17, 2013

(86) PCT No.: PCT/US2013/060074
§ 371 (c)(1),
(2) Date: Mar. 17, 2015

(87) PCT Pub. No.: WO2014/043668
PCT Pub. Date: Mar. 20, 2014

(65) Prior Publication Data
US 2015/0247908 A1    Sep. 3, 2015

Related U.S. Application Data

(60) Provisional application No. 61/701,810, filed on Sep. 17, 2012.

(51) Int. Cl.
*G01R 33/48* (2006.01)
*A61B 5/055* (2006.01)
(Continued)

(52) U.S. Cl.
CPC .......... *G01R 33/4828* (2013.01); *A61B 5/015* (2013.01); *A61B 5/055* (2013.01); *G01R 33/4804* (2013.01); *G01R 33/485* (2013.01)

(58) Field of Classification Search
CPC .... A61B 5/015; A61B 5/055; G01R 33/4828; G01R 33/4804; G01R 33/485
(Continued)

(56) References Cited

U.S. PATENT DOCUMENTS 4,847,559 A    7/1989    Keren
5,414,358 A    5/1995    Eilenberg et al.
(Continued)

FOREIGN PATENT DOCUMENTS

JP    2003-019124 A    1/2003
WO    WO 2012143491 A1 * 10/2012    ........... G01R 33/465

OTHER PUBLICATIONS

Kuroda et al. (Temperature Mapping Using the Water Proton Chemical Shift: Self-Referenced Method With Echo-Planar Spectroscopic Imaging; Feb. 2000; Magnetic Resonance in Medicine; Edition 43; pp. 220-225).*
(Continued)

*Primary Examiner* — Melissa J Koval
*Assistant Examiner* — Rahul Maini
(74) *Attorney, Agent, or Firm* — Johns Hopkins Technology Ventures

(57) ABSTRACT

An embodiment in accordance with the present invention provides a method of non-invasively detecting and imaging temperature or temperature changes by assessing the temperature induced shifts in the saturation spectrum of water
(Continued)

using MRI, namely saturation shift referencing. This procedure includes the MRI procedures to assess water saturation spectrum and the data processing steps to determine the temperature induced shifts of water resonance frequency and consequently to estimate the temperature change. This procedure also includes the procedure of assessing fat saturation spectrum and estimating fat resonance frequency. This method can be used as a clinical procedure for temperature mapping in multiple applications, especially where a significant amount of fat is present. One application is to monitor the temperature of the targeted tumor and its surrounding tissues during the procedure of hyperthermia. Such local hyperthermia can be applied, using high-intensity focus-ultrasound for deep-seated tissues or heating supplies for superficial tissues.

20 Claims, 8 Drawing Sheets

(51) Int. Cl.
*A61B 5/01* (2006.01)
*G01R 33/485* (2006.01)

(58) Field of Classification Search
USPC .......................................................... 324/309
See application file for complete search history.

(56) References Cited

U.S. PATENT DOCUMENTS

| | | | | |
|---|---|---|---|---|
| 5,842,989 | A | * | 12/1998 | Zur ........................ A61B 5/055 324/306 |
| 8,536,866 | B2 | | 9/2013 | Van Zijl et al. |
| 2009/0142273 | A1 | * | 6/2009 | Pagel .................. G01R 33/5601 324/307 |
| 2010/0286502 | A1 | * | 11/2010 | Van Zijl ............... G01R 33/483 600/410 |
| 2012/0019245 | A1 | | 1/2012 | Reddy et al. |
| 2015/0051475 | A1 | * | 2/2015 | Leussler ............ G01R 33/4804 600/411 |
| 2015/0190659 | A1 | * | 7/2015 | Kohler ............... G01R 33/5611 600/411 |

OTHER PUBLICATIONS

Bley et al. ("Fat and Water Magnetic Resonance Imaging"; 2009; Journal of Magnetic Resonance Imaging; 31:4-18) (Year: 2009).*
Soher et al. ("Noninvasive Temperature Mapping With MRI Using Chemical Shift Water-Fat Separation"; 2010; Magnetic Resonance in Medicine; 63:1238-1246) (Year: 2010).*
Kim, M., et al., "Water saturation shift referencing (WASSR) for chemical exchange saturation transfer (CEST) experiments" Magn Reson Med (2009), vol. 61, No. 6, pp. 1441-1450.
Liu, G., et al., "High-throughput screening of chemical exchange saturation transfer MR contrast agents", Contrast Media Mol Imaging (2010), vol. 5, No. 3, pp. 162-170.

* cited by examiner

NON-INVASIVE TEMPERATURE MAPPING USING TEMPERATURE-RESPONSIVE WATER SATURATION SHIFT REFERENCING (T-WASSR) MRI

CROSS-REFERENCE TO RELATED APPLICATIONS

This application is a 35 U.S.C. § 371 U.S. national entry of International Application PCT/US2013/060074, having an international filing date of Sep. 17, 2013, which claims the benefit of U.S. Provisional Application No. 61/701,810, filed Sep. 17, 2012, the content of each of the aforementioned applications is herein incorporated by reference in their entirety.

GOVERNMENT SPONSORSHIP

This invention was made with government support under R21EB008769, R21EB015609, R01EB015031, R01EB015032, P41EB015909 awarded by the National Institutes of Health. The government has certain rights in the invention.

FIELD OF THE INVENTION

The present invention relates generally to magnetic resonance imaging. More particularly, the present invention relates to a method of magnetic resonance imaging.

BACKGROUND OF THE INVENTION

Magnetic resonance imaging (MRI) has long been used to create detailed internal images for use in medical diagnostics and treatment as well as studies of the brain and body. In MRI, a powerful magnetic field is used to align the magnetization of atomic nuclei in the body, and radio frequency is used to alter the alignment of the magnetization. The nuclei then produce a rotating magnetic field that is detectable by an MRI scanner and recordable to create images of the scanned area of the body. Over the years, various techniques have been developed to perform MRI scans that produce images for specialized diagnostics.

It is of great clinical interest to measure the temperature changes of deep-seated tissues non-invasively during the course of cancer thermotherapy (hyperthermia or high temperature thermal ablation), hypothermia treatment of acute ischemic stroke, and during triggered drug release from temperature-sensitive drug delivery systems. To date, a number of MRI techniques have been suggested for assessing temperature through, in addition to using temperature-sensitive MRI contrast agents, monitoring a particular MRI property that is responsive to temperature changes, including proton density, diffusion constants, $T_1$ and $T_2$ relaxation times, magnetization transfer ratio, and, the most widely used, water proton resonance frequency (PRF). Water PRF shifts are sensitive to temperature because it strongly affects the chemical shift of water protons by altering their hydrogen bonding state. Water PRF-based temperature measurement is plausible because of its relatively high sensitivity (−0.01 ppm/° C.) over a wide range of temperatures (−15 to 100° C.), which is tissue-type-independent except for adipose tissue. Water PRF methods using MRI have been implemented with two techniques, MR spectroscopic (MRS) imaging, and gradient-echo based phase mapping. Proton MRS directly determines the chemical shift of water protons by assessing the 1H NMR spectrum of the region of interest. Using non-temperature-responsive methyl and methylene protons (e.g. from N acetyl aspartate (NAA) or lipid) as reference, the absolute temperature can be determined after calibration. However, this technique is often limited by a low spatial or temporal resolution, and as such, not suitable for real-time monitoring. Alternatively, a high-resolution temperature change map can be obtained by assessing the difference in phase maps between two temperatures. To date, it is the most widely used non-invasive MRI method for temperature mapping in clinical and preclinical studies, with a capability of monitoring temperature change in real-time. However, the accuracy of measurement may be complicated when magnetic background gradient effects (e.g. due to changing shims) cannot be neglected or a significant portion of fat is present.

Recently, a so-called Water Saturation Shift Referencing (WASSR) method (30) was proposed to determine $B_0$ shifts by assessing the minimum of the water direct saturation (DS) spectrum using a weak radiofrequency saturation. In such an approach, the $B_0$ shift of each voxel is simply determined from a DS spectrum by finding the frequency that corresponds to the maximum saturation (or the weakest water signal intensity), using either a non-model-based maximal symmetry algorithm or a model-based Lorentzian line shape algorithm. The latter is possible because the steady-state direct saturation spectrum can be described exactly by a Lorentzian line shape.

It would therefore be advantageous to provide a method of MRI to map temperature changes if the temperature is the dominating factor causing the shift in $B_0$. It would also be advantageous to provide a WASSR based temperature mapping MRI method, that can directly determine the chemical shift of water protons, similar to an MRS method, but with a higher temporal and spatial resolution and allow an unbiased assessment of water PRF in the presence of lipid protons without the need of a priori knowledge of fat composition and additional data processing steps.

SUMMARY OF THE INVENTION

The foregoing needs are met, to a great extent, by the present invention, wherein in one aspect a method for obtaining a magnetic resonance image spectrum of a subject includes performing a temperature-responsive water saturated shift referencing (T-WASSR) experiment of the subject using an MRI machine to measure a chemical shift of water protons. The method also includes determining a water peak in the presence of a lipid proton, wherein the water peak is separated from that of the lipid proton. Additionally, the method includes assessing a proton resonance frequency of water (water PRF).

In accordance with an aspect of the present invention, the method further includes creating an image of at least a portion of the subject using the water PRF. The image can depict temperature and temperature-induced shifts. The method also includes mapping the temperature of fat containing tissue. Fat resonance frequency can also be measured and subsequently used to provide an internal reference to account for the field shift caused by non-temperature related factors. Absolute temperature of the fat containing tissue can also be measured with the method. Additionally, the method can include determining a maximum of frequency for water direct saturation spectrum at various temperatures. This can further be determined using a Lorentzian line shape. The method can also include calculating a change in temperature using the difference in water PRF shifts.

In accordance with another aspect of the present invention, a system for obtaining a magnetic resonance image spectrum of a subject includes a magnetic resonance imaging (MRI) machine configured to obtain the magnetic resonance image spectrum of the subject. The system also includes a non-transitory computer readable medium programmed to perform a temperature-responsive water saturated shift referencing (T-WASSR) experiment of the subject. Additionally the non-transitory computer readable medium is programmed to measure a chemical shift of water protons, determine a water peak in the presence of a lipid proton, wherein the water peak is separated from that of the lipid proton, and assess a proton resonance frequency of water (water PRF).

BRIEF DESCRIPTION OF THE DRAWINGS

The accompanying drawings provide visual representations, which will be used to more fully describe the representative embodiments disclosed herein and can be used by those skilled in the art to better understand them and their inherent advantages. In these drawings, like reference numerals identify corresponding elements and:

FIG. 1A is an illustration of measuring temperature-induced water PRF shifts using T-WASSR. FIG. 1B illustrates the measurement error (Hz) as a function of SNR level at the spectral resolution ranging from 2 to 20 points per FWHM. FIG. 1C illustrates the measurement error (Hz) as a function of resolution (points per FWHM) at the SNR levels of 25, 50 and 75 respectively. FIG. 1D illustrates the measurement error (Hz) as a function of linewidth (FWHM) at the SNR levels of 25, 50 and 75 respectively. FIG. 1E illustrates the measurement error (Hz) as a function of resolution (points per FWHM) for the sweepwidth ranging from 2 to 8 times of FWHM. Dashed lines in FIGS. 1B, 1C, 1D, and 1E correspond to 1 Hz error. The error bars shown in FIGS. 1C, 1D, and 1E were the standard deviations of the fitting errors of 30 repeated simulations. FIG. 1F illustrates the fitting of the water DS spectra and the corresponding "true" DS spectra. The data set of discretely-sampled and noise-superimposed spectral data was simulated from the 'true' data using an SNR level of 75, a spectral resolution of 4 points per FWHM and a sweepwidth of SW/FWHM=2.

FIGS. 2A and 2B illustrate measured maps of temperature changes using phase imaging and the T-WASSR method at 300K, 305K, 310K, 315K, and 320K using an NMR thermocouple. FIG. 2C illustrates a linear regression plot showing good correlation between the measured temperature changes, and FIG. 2D illustrates a Bland-Altman plot showing a good level of agreement between the two methods.

FIG. 3A illustrates a $T_{2-w}$ image of the phantom and the ΔT maps obtained by T-WASSR and phase mapping for a temperature change from 310K to 316K using an NMR termocouple. FIG. 3B illustrates a comparison between $^1$H NMR spectra measured using a single-voxel localized MRS (PRESS) method and the T-WASSR spectra (both around the water proton resonance and fat proton resonance) of an ROI containing only cheese. FIG. 3C illustrates a comparison between the measured mean ΔT of both agarose ROI (blue) and cheese ROI (red) obtained by T-WASSR and MRS, respectively. The temperature was increased from 297K to 316K using an NMR thermocouple. FIG. 3D illustrates for the cheese region containing both fat and water, maps of the chemical shift difference (Jδ) between water PRF and lipid PRF (top panel) were calculated at each temperature. The mean ROI Jδ with respect to the absolute temperature (NMR thermocouple readings) is displayed in the bottom panel. The error bars are the standard deviation of the calculated Jδ for the ROI.

FIG. 4A illustrates a $T_{2-w}$ image (left) and measured temperature maps (right), using both T-WASSR and phase imaging, 30 minutes after the temperature of circulating water was set to 318K (45° C., $T_1$) and 328K (55° C., $T_2$), respectively. FIG. 4B illustrates the WASSR spectra of a muscle ROI of the right leg of a mouse (yellow box in the $T_{2-w}$ image in FIG. 4A before heating (T(0), red) and after heating to temperature T(1) (green) and temperature T(2) (blue). Solid lines show the Lorentzian fitting; dashed lines show the fitted water PRF for each temperature. FIG. 4C illustrates a quantitative comparison of the measured temperature changes using two methods. ROI1 is the same ROI used in FIG. 4B and ROI2 is a small region indicated by the red arrow on the $T_{2-w}$ image, where a very high temperature increase was observed.

DETAILED DESCRIPTION

Figure 1A:
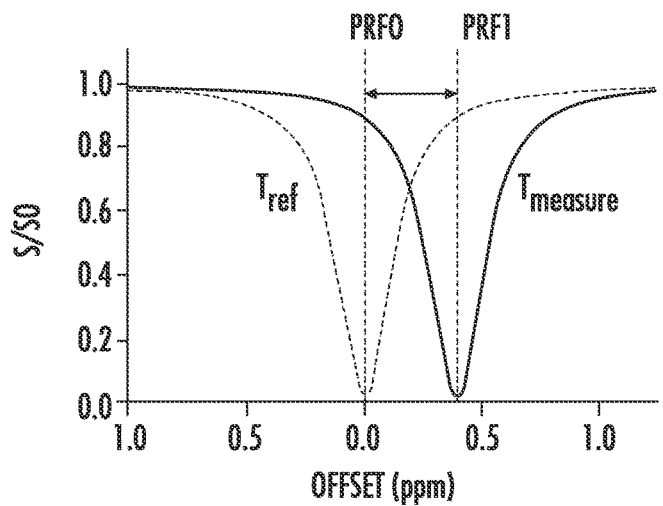
FIGS. 1A-1F illustrate simulations showing the T-WASSR measurement of water PRF shift.

The presently disclosed subject matter now will be described more fully hereinafter with reference to the accompanying Drawings, in which some, but not all embodiments of the inventions are shown. Like numbers refer to like elements throughout. The presently disclosed subject matter may be embodied in many different forms and should not be construed as limited to the embodiments set forth herein; rather, these embodiments are provided so that this disclosure will satisfy applicable legal requirements. Indeed, many modifications and other embodiments of the presently disclosed subject matter set forth herein will come to mind to one skilled in the art to which the presently disclosed subject matter pertains having the benefit of the teachings presented in the foregoing descriptions and the associated Drawings. Therefore, it is to be understood that the presently disclosed subject matter is not to be limited to the specific embodiments disclosed and that modifications and other embodiments are intended to be included within the scope of the appended claims.

An embodiment in accordance with the present invention provides a system and method of non-invasively detecting and imaging temperature or temperature changes by assessing the temperature induced shifts in the saturation spectrum of water using MRI, namely saturation shift referencing. This method includes the MRI procedures to assess water saturation spectrum and the data processing steps to determine the temperature induced shifts of water resonance frequency and consequently to estimate the temperature change. This method also includes the procedure of assessing fat saturation spectrum and estimating fat resonance frequency. This method can be used as a clinical procedure for temperature mapping in multiple applications, especially where a significant amount of fat is present. One application is to monitor the temperature of the targeted tumor and its surrounding tissues during the procedure of hyperthermia. Such local hyperthermia can be applied, using high-intensity focus-ultrasound for deep-seated tissues or heating supplies for superficial tissues.

In accordance with the present invention an MRI system can be used to implement the method described herein. Such a system would include a magnetic resonance imaging (MRI) machine networked either wired or wirelessly to a computing system or a server. The MRI machine can take the form of any suitable machine known to or conceivable by one of skill in the art. In addition the computing device can be directly incorporated into the MRI machine or can be in communication with the control platform for the MRI machine. The computing can conceivably be programmed or contain a non-transitory computer readable medium programmed with the protocol for the imaging method described herein, and can also be configured for receiving and analyzing the resultant images. Any other suitable computing device configuration known to or conceivable by one of skill in the art could also be used, and the examples given here are not to be considered limiting.

At a given temperature (T), the apparent temperature-dependent water proton chemical shift $\delta(T)$ is determined by $$\delta(T)=\delta_0+\delta_T(T) \quad [1]$$

where $\delta_0$ is the sum of temperature-independent contributions, including the inherent chemical shift and the shift that arises from local $B_0$ field inhomogeneity, and $\delta_T(T)$ is the temperature-dependent shift contribution, which changes linearly with respect to the change in temperature, i.e., $\Delta\delta_T(T)=\alpha\Delta T$, where the temperature coefficient $\alpha(=d\delta/dT)$ is approximately $-0.01$ ppm/° C. for most tissues except fat.

In MRI measurements, $\delta(T)$ is determined by measuring the local magnetic field, $B_{loc}$, with the relationship $$B_{loc}(T) = \left(1 + \delta(T) - \frac{2}{3}\chi(T)\right)B_0, \quad [2]$$

where $B_0$ is the magnetic field strength and $\chi(T)$ is the temperature-dependent tissue susceptibility. The temperature-dependent susceptibility constant, however, is much smaller than the constant of temperature-dependent PRF shift for pure water and tissues with high water content such as muscle, making the contribution of the temperature-dependent susceptibility effect to the local magnetic field less 10% than that of water PRF. Thus, it is generally assumed that the temperature-dependent susceptibility can be neglected in most applications.

In the case of phase mapping, the image phase $\Phi(T)$ is determined by the water PRF $\delta(T)$, assuming there is a negligible temperature-dependent tissue susceptibility change and a perfect scanner offset frequency:

$$\Phi=\gamma T_E(B_{loc}-B_0)=\gamma T_E\delta(T)B_0 \quad [3]$$

where $\gamma$ is the gyromagnetic ratio of water protons (42.58× 106 Hz/Tesla) and $T_E$ is the echo time used in a gradient echo pulse sequence. To eliminate the contribution of the temperature independent term $\delta 0$ from $\delta(T)$, image phases at two temperatures, the temperature to be measured ($T_{measure}$) and a reference temperature ($T_{ref}$), are compared to calculate the temperature change ($\Delta T$) between them:

$$\Delta T=T_{measure}-T_{ref}=[\Phi(T_{measure})-\Phi(T_{ref})]/\alpha\gamma T_E B_0 \quad [4]$$

Derived from Bloch equations of a single water pool model, the analytical solution of the observed water longitudinal magnetization at the steady state ($M_z^{ss}$), in the presence of a saturation pulse with a $B_1$ field strength of $\omega_1$ (in the unit of radian), at a particular offset ($\Delta\omega=\omega_0-\omega_{RF}$), is given by $$M_z^{ss} = \frac{M_z^0}{1 + \left(\frac{\omega_1}{\omega_0 - \omega_{RF}}\right)^2 \left(\frac{T_1}{T_2}\right)} \quad [5]$$

where $\omega_0$ and $\omega_{RF}$ are the resonant frequency of water protons and the saturation frequency of the applied RF pulse, respectively, $M_z^0$ is the longitudinal magnetization without saturation, and $T_1$ and $T_2$ are the spin-lattice and spin-spin relaxation times of water, respectively. Eq. [5] thus provides a mathematic model of the frequency dependence of the water DS spectrum described by a Lorentzian line shape. The maximum saturation occurs when the RF pulse is applied at offset $\omega_0=\omega_{RF}$, which provides a practical way to measure $\omega_0$ by sweeping $\omega_{RF}$. When discrete and noise-carrying experimental data are used, however, data fitting has to be performed using a non-model based or model-based algorithm. It should also be noted that the presence of Magnetization Transfer (MT) and/or Chemical Exchange Saturation Transfer (CEST) may compromise the single-pool assumption, especially when applied to in vivo measurements. Fortunately, as shown previously, implementation with a weak RF saturation pulse may effectively minimize the impact of MT and CEST. Similarly to Eq. [4], and illustrated in FIG. 1A, temperature changes can be determined by comparing the water PRF ($\omega_0$) determined for each pixel in the $B_0$ shift map at two temperatures:

$$T_{measure}=T_{ref}+\Delta T=T_{ref}+(\omega_0(T_{measure})-\omega_0(T_{ref}))/2\pi\cdot\alpha\gamma B_0 \quad [6]$$

All simulations were performed using MATLAB (Mathworks, Natick, Mass.). The saturation parameters used for all simulations were a continuous wave (CW) pulse with a duration of 0.5 seconds and a $B_1$ field strength of $\omega_1/2\pi=21.3$ Hz. The simulated raw data to be used for testing the proposed Lorentzian fitting algorithm was produced in two steps. First, saturation frequency-dependent DS spectral data sets were created using a steady-state analytical solution with the frequency range from −500 Hz to 500 Hz. A fixed $T_1$ relaxation time of 1.4 sec (adapted from literature for muscle at 3T) was used, whereas $T_2$ relaxation times were varied from κ to 500 msec to produce DS spectra with different linewidth. The full width at half maximum (FWHM) of each spectrum was experimentally measured based on the DS spectrum. All spectra were shifted by 50 Hz to resemble a water PRF shift (or $B_0$, true) of 50 Hz. The second step was to create 'real' data that was discretely sampled and noise-superimposed. First, the 'true' data sets produced in the first step were asymmetrically segmented into new data sets from −450 to +550 Hz, with their spectral resolution ranging from 2 to 20 sampling points per FWHM to resemble discrete data sampling. Subsequently, random white noise, at a signal-to noise ratio (SNR) level ranging from 20:1 to 150:1, was produced and superimposed on each "discretely sampled" and "$B_0$-shifted" data set.

Finally, the data sets were segmented symmetrically around the resonance offset with a sweepwidth (SW) varying from 2 times to 8 times the FHWM. These final data sets were then fitted to Eq. [5] to estimate the $B_0$ shift of the spectrum, i.e., $B_{0,estimated}$. The error of fitting was calculated by $|B_{0,estimated}-B_{0,true}|$, where $B_{0,true}=50$ Hz in our simulations. Considering that the noise was randomly produced for each given SNR level and spectral resolution, we calculated the mean measurement error of thirty data sets that were produced in step 2 separately. Finally, the mean and standard deviation of fitting errors were plotted with respect to SNR, spectral resolution (points per FWHM) and sweepwidth (SW/FWHM).

Two phantoms were prepared for in vitro temperature measurements. The first phantom contained only agarose gel to represent non-fat-containing tissues and was prepared by filling a 5 mm NMR tube with 1 ml 2% low melting point agarose gel (Sigma, St Louis, Mo., doped with Gd-DTPA to reduce the $T_1$ relaxation time). The second phantom contained a piece of cheese (8.9% fat, Saputo Cheese, USA Inc., Lincolnshire, Ill.) to resemble fat-containing tissues that was immersed in 2% melted agarose solution (~50° C.) in a 10 mL plastic vial, then cooled down to room temperature.

The in vitro MRI acquisition was performed on a vertical bore 11.7 Tesla Bruker Avance system equipped with a 15 mm birdcage RF coil. A NMR thermocouple was used to control the temperature by blowing heating gas to the samples. For the phantom containing only agarose gel, the intra-bore temperature was adjusted from 300K to 320K (47° C.) at 5K increments. For the phantom that mimicked fat-containing tissues, the intrabore temperatures were set to 302K, 310K, and 313K in addition to the initial room temperature (without heating, measured as 297K). There was always 30 minutes waiting period each time after the thermocouple was adjusted to the next temperature. The T-WASSR images at each temperature were acquired using a modified Rapid Acquisition with Relaxation Enhancement (RARE) sequence (RARE factor=16, slice thickness=1 mm, TR=1.5 sec, TE=5 ms, acquisition matrix size=128×128, which corresponds to 80 phase encoding steps when a 1.6 partial Fourier transform (FT) acceleration is used; spatial resolution=80×80 [m, and the number of averages (NA)=1). The saturation of water or lipid protons was implemented using a single continuous wave (CW) RF pulse ($t_{sat}$=500 ms, $B_1$=0.5 μT ($\omega_1/\pi$=21.3 Hz)), with saturation offsets swept from −0.5 ppm to +0.5 ppm with respect to the water resonant frequency at a resolution of 0.1 ppm. To acquire the direct saturation spectrum of lipid protons, the saturation offset was swept from −3 ppm to −4 ppm with respect to the water resonance frequency, with the same increment of 0.1 ppm. The total acquisition time for each water (or fat) DS spectrum acquisition was two minutes.

Phase map at each temperature was acquired using a multiple gradient echo method, implemented with a Fast Low Angle SHot Magnetic Resonance Imaging (FLASH) sequence (flip angle=30°, TR=200 ms, 128 phase encoding steps and number of averages=4) with TE=2.5 ms, 5 ms, 7.5 ms, 10 ms, and 12.5 ms, which allowed the calculation of phase maps with a temporal phase unwrapping algorithm. The total acquisition time was 1.8 minutes (NA=4). 1H NMR spectra of the regions of interest were acquired using a point-resolved spectroscopy (PRESS) sequence (TR/TE=3000/21 ms, spectrum acquisition size=2048 points, sweep width=6.0 kHz, and number of averages=32). The acquisition time was 1.52 minutes. 1H NMR spectra were processed using 1D FT with a line-broadening factor of 2, followed by phase and baseline correction using the Topspin software package (Bruker Biopsin Co., Billerica, Mass.).

All animal experiments were approved by institutional animal care and use committee (IACUC). Eight-week old female C57BL/6.SJL mice were purchased from Jackson Labs (Bar Harbor, Me.). The right leg of the mouse was wrapped with a heating pad with circulating water. Insulation material was placed between the left leg and the heating pad. After appropriately positioning the mouse in the scanner, the lower limbs of the mouse were assessed using both T-WASSR and phase mapping. Three measurements were performed: at room temperature (T(0)=24° C.) where the water circulation pump was not turned on, and during hyperthermia where the temperature of circulating water was maintained at T(1)=45° C. and T(2)=55° C. using a thermostat. There was always 30 minutes waiting period each time after the thermostat was set at a new temperature. In vivo images were collected on a 9.4 T Bruker scanner using a 25 mm sawtooth resonator. The same imaging scheme as that for in vitro imaging was used, except the RARE factor was reduced to 8 and a frequency-selective fat suppression pulse was used (hermite pulse, pulse length=3.4 ms and offset=−3.5 ppm). The saturation offsets were swept from −2 ppm to +2 ppm with 0.1 ppm steps. We employed a keyhole approach to reduce the acquisition matrix from 128×128 to 128×64, which resulted in a 12-sec acquisition time per image or a total acquisition per WASSR spectrum of approximately eight minutes. The same phase-mapping procedure as that described above was also conducted immediately after each T-WASSR acquisition.

All data were processed using custom-written MATLAB scripts. Images were first filtered by a SNR>40 to remove low SNR pixels, with the noise estimated by the standard deviation of an ROI containing pure noise (often the black regions at the upper right corners) of the $S_0$ image. For the T-WASSR approach, the $B_0$ maps at each temperature were first calculated by fitting the T-WASSR spectrum to Eq. [5]. Subsequently, the temperature change map was calculated by converting the $B_0$ difference (Hz), pixel-wise, between two temperatures, to temperature (K) using Eq. [6]. When a keyhole approach was used, the skipped 64 high spatial-frequency k-space lines in the raw data of each WASSR spectral image were substituted by the corresponding lines in a reference image that was acquired with the full sampling size (i.e., 128 phase-encoding steps). The raw data were then reconstructed and processed using the procedure described above. For phase mapping, temperature change maps were produced by directly comparing phase images at the two temperatures according to Eq. [4].

Correlation analysis was performed using linear regression of the measured temperatures of the same subject between the proposed T-WASSR method and phase-mapping or MRS method. In addition, Bland-Altman analysis was performed to assess the agreement between the T-WASSR method and phase mapping in measurements of the agarose gel phantom, with a criteria of 95% of the standard deviation of the differences between the two methods. A pixel-by-pixel Student's t-test (two-tailed, unpaired) was performed to compare two specific ROIs of the temperature maps obtained by T-WASSR and phase mapping, respectively.

Figure 1B:
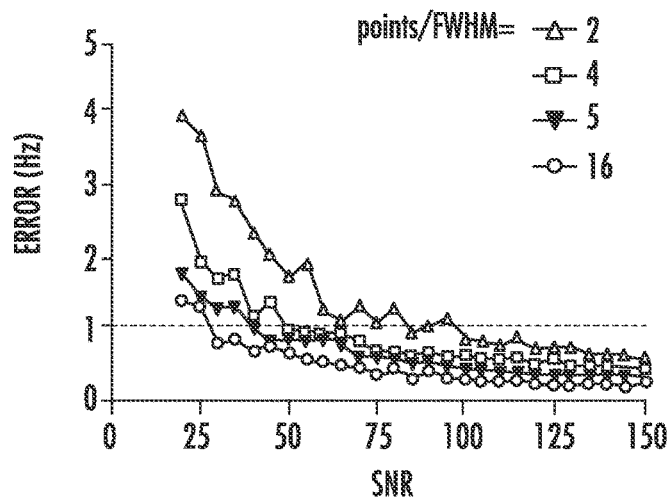
Figure 1C:
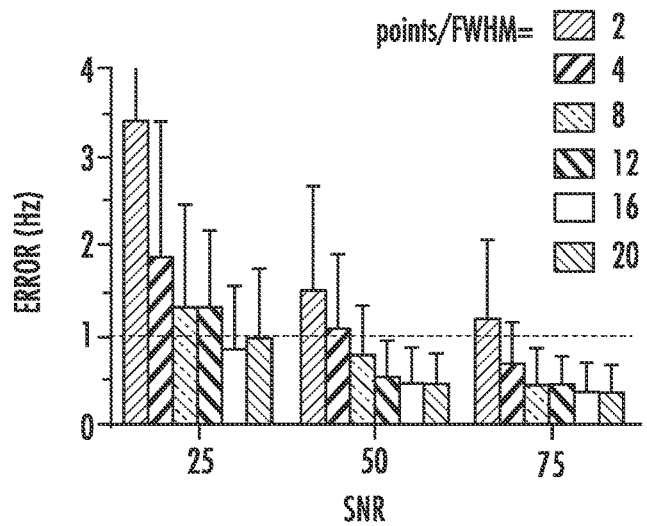

To examine whether the proposed Lorentzian fitting algorithm could provide an accurate estimation of water PRF, the fitting was performed on the simulated data with full width half maximum (FWHM) of 127 Hz ($T_2$=5 msec). FIG. 1B shows that either increasing the SNR or increasing the sampling size improves the accuracy of estimating water PRFs, however, at the expense of an increased acquisition time. To estimate the minimal sampling size for a reliable fitting (i.e., error <1 Hz or relative error <2%), we investigated the mean measurement error as a function of points per FWHM at three SNR levels (i.e., 75, 50 and 25, FIG. 1C). The result clearly shows that the choice of spectral resolution greatly relies on the SNR. In particular, 2 points per FWHM would be adequate for high SNR (i.e. >75), while 4 and 8 points per FWHM should be considered for moderate (~50) and low SNR (~25), respectively.

Figure 1D:
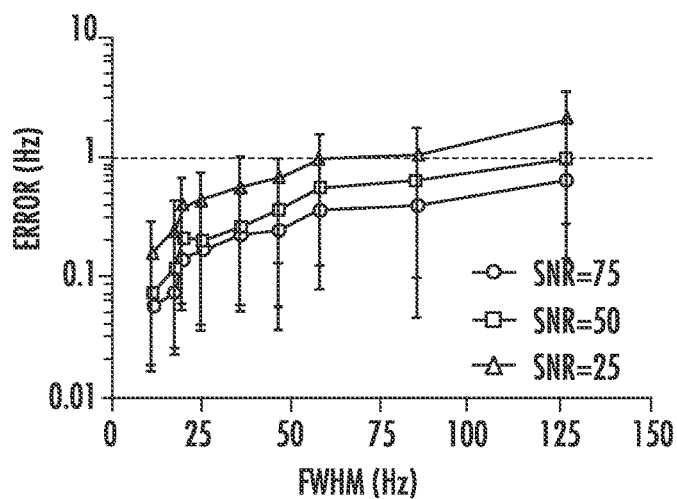
Figure 1E:
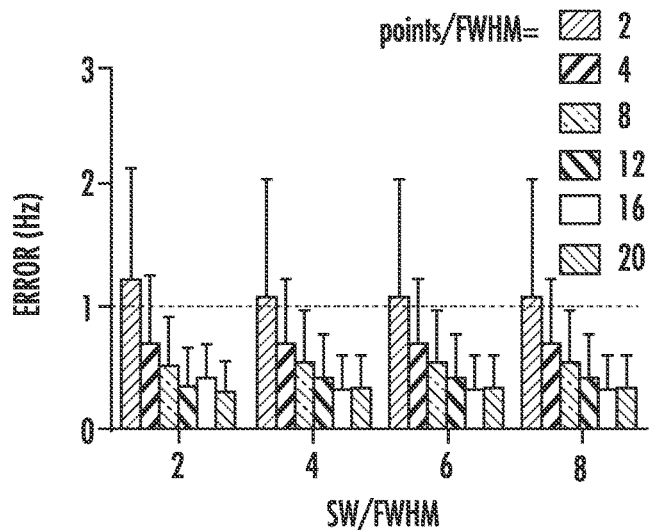

Next, the influence of linewidth and the choice of sweepwidth were examined. As expected, the results (FIG. 1D) show that the mean measurement error dramatically increases with linewidth, indicating a larger sampling size should be used for in vivo applications where the spectral linewidth is generally broad. In general, a sufficiently broad sweepwidth should always be used in order to cover the complete range of $B_0$ inhomogeneity over the image slice. However, in the case that only some regions are of interest and their $B_0$ shifts are known, reducing the sweepwidth could be considered to accelerate the acquisition. This strategy is particularly useful for monitoring the temperature changes of a particular tissue during the procedure of hyperthermia where the $B_0$ shifts before the procedure are known and the subsequent changes are within a range <1 ppm (~0.01 ppm per ° C.). FIG. 1E shows that no significant reduction of measurement accuracy is found when the sweepwidth was increased from 2 to 8 times of FWHM, indicating that the requirement of 2 points resolution per FWHM is needed.

Figure 1F:
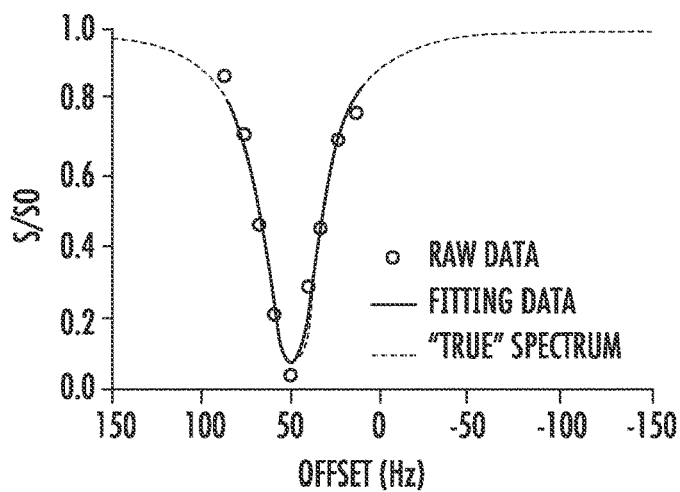

Collectively, the minimal sampling size for acquiring a T-WASSR data set is: 2, 4 or 8 points per FWHM for high, moderate, or low SNR respectively. The sweepwidth generally should be large enough to cover the entire $B_0$ range, however, could be reduced to up to SW/FWHM=2 for the cases that only the temperature changes of particular regions with known $B_0$ shifts are under monitoring. FIG. 1F presents an example of the fitting of the simulated data ($T_2$=50 msec, FWHM=36 Hz) using a SNR of 50 and a spectral resolution of 4 points per FWHM. The systematic error between the estimated water PRF and the 'true' value was less than 1 Hz, corresponding to a 0.8° C. error in temperature at 3T (128 MHz) or 0.25° C. or less at a field strength higher than 9.4T (400 MHz).

Figure 2A:
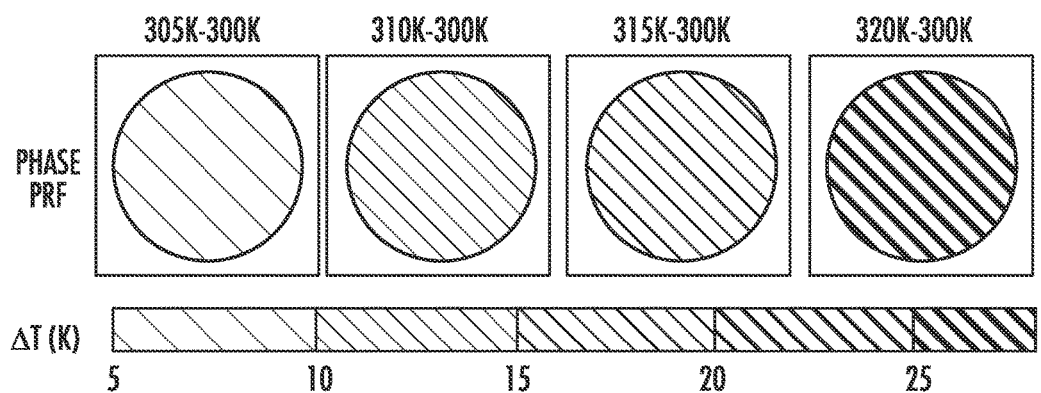
FIGS. 2A-2D illustrate the correlation between T-WASSR and traditional phase-based PRF imaging for measuring the temperature change of water in an agarose gel phantom.
Figure 2B:
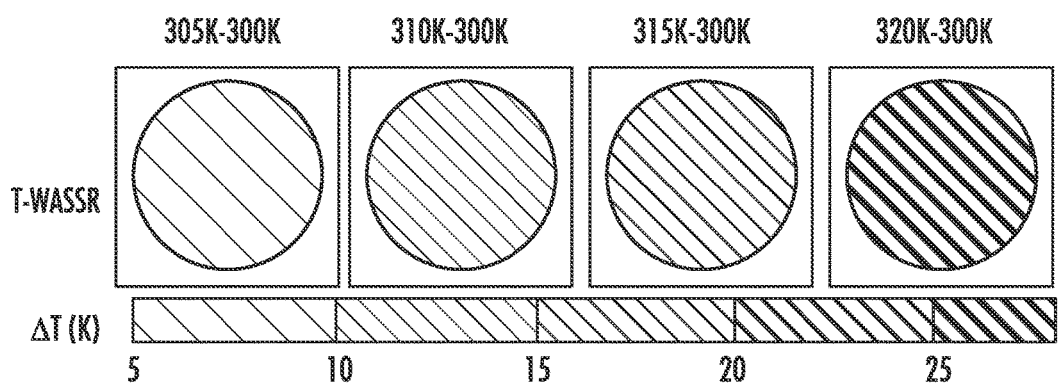
Figure 2C:
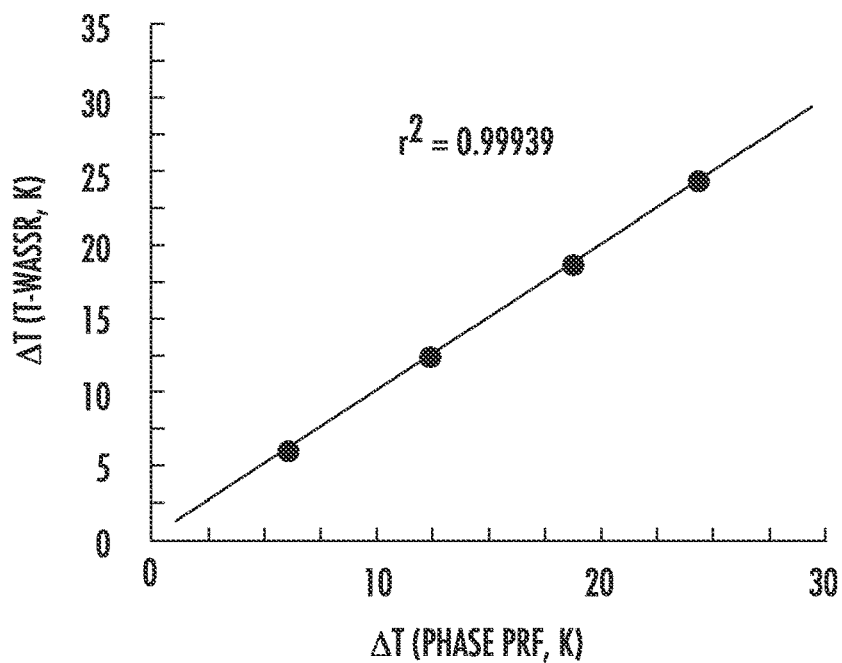
Figure 2D:
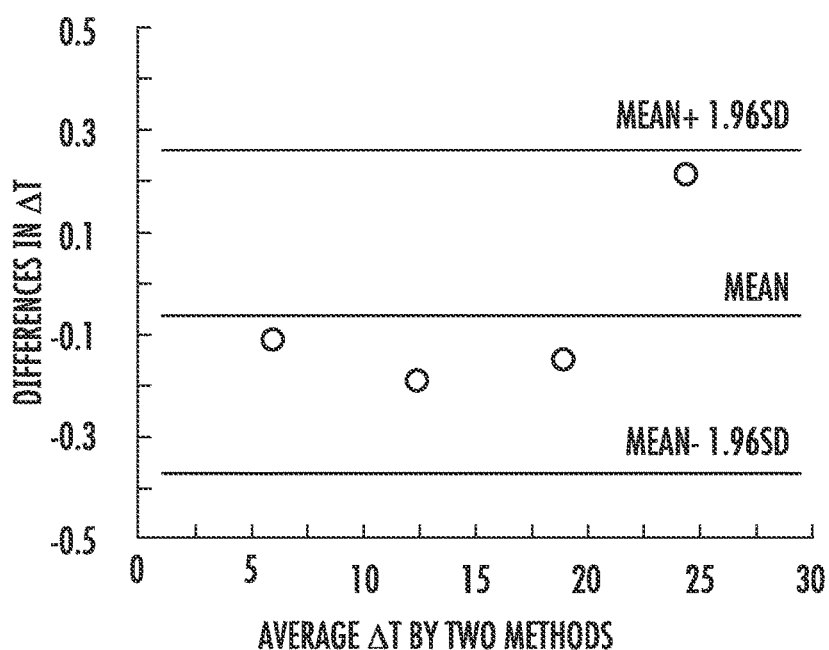

The T-WASSR method was compared to the conventional phase mapping based PRF method using an agarose gel phantom. FIGS. 2A and 2B show that both T-WASSR and phase PRF imaging provide high-resolution temperature maps when the sample temperature was increased from 300K to 320K using an NMR thermocouple. Similar to phase mapping, T-WASSR can report on only the relative changes in temperature (ΔT) and not the absolute temperature except when an internal reference is available. The quantitative comparison between the two methods was performed using the mean ΔT of the ROI that covered the entire sample. In addition to the good linear correlation (r2=0.999, FIG. 2C), there is good agreement between the two methods according the Bland-Altman plot (FIG. 2D). It is evident that, at each temperature, the difference between the two measurements falls into the region within 95% of the standard deviation of the differences between the two methods. Both methods were capable of mapping temperature changes at a high spatial resolution of 80×80 m in the current study. With regard to the temporal resolution, the total acquisition time for a complete T-WASSR measurement used in this study was two minutes, which is comparable to that of multiple gradient echo phase mapping. It should be noted that the acquisition time of T-WASSR was reduced in such a way that a portion of k-space lines were skipped (i.e., 80 instead of 128 phase encoding steps) and no signal averaging was used.

Figure 3A:
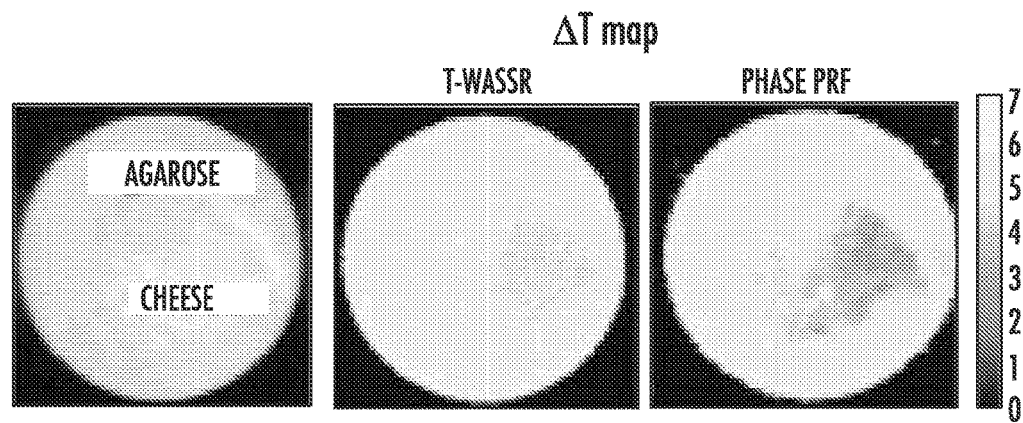
FIGS. 3A-3D Measuring temperature change (ΔT) in a phantom containing both fat and water using T-WASSR.
Figure 3B:
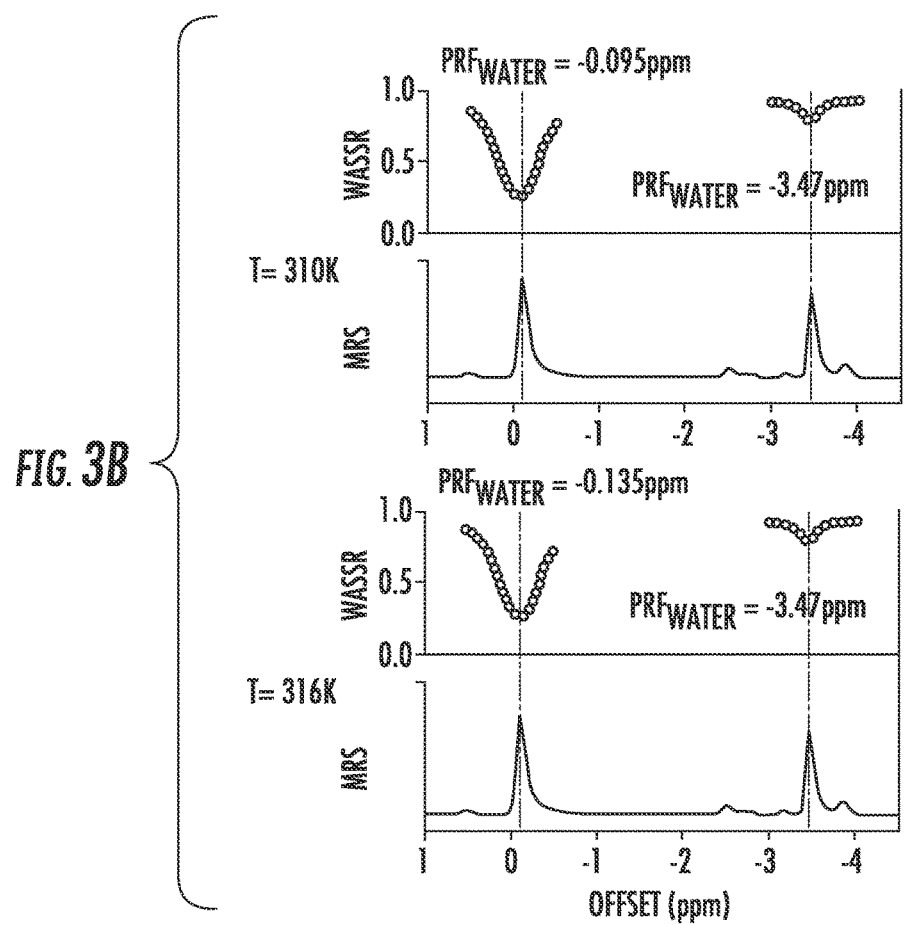
Figure 3C:
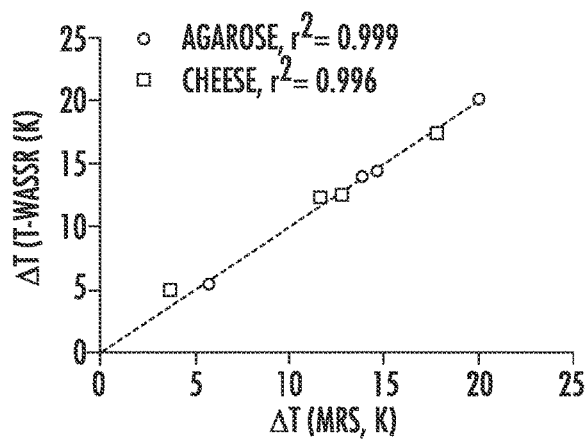
Figure 3D:
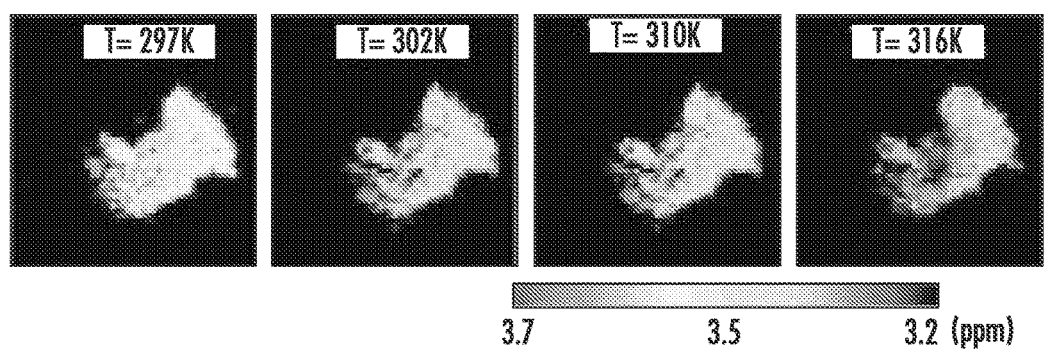
Figure 3D:
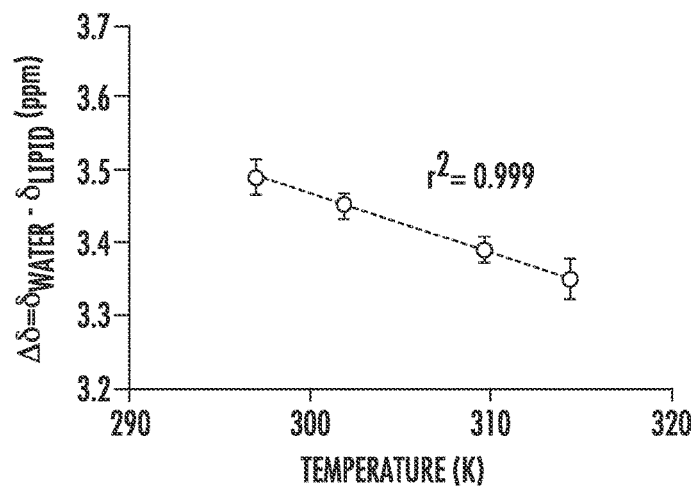

To investigate whether the T-WASSR method could be applied to monitor the temperature of tissues containing fat, a cheese phantom composed of both water and fat (8.9% w/w) was used. As shown in FIG. 3A, when the nominal temperature of the sample was elevated from 310K (37° C.) to 316K (43° C.), T-WASSR provided steady temperature mapping, of both regions containing water only and regions containing both a mixture of water and fat, with a mean ΔT of 5.7K and 4.6K for the agarose and cheese ROI, respectively. These results are consistent with the ΔT calculated using the water PRF shifts determined by the single-voxel MRS method (5.6 K and 5.0 K for the voxel containing agarose and that containing cheese, respectively, FIG. 3B). In contrast, the phase mapping provided a clearly deviating mean ΔT for the cheese ROI (3.4K), but a consistent measurement for the agarose ROI (5.3K). Good correlation (r2=0.999) was revealed between ΔT measured by the two methods for both the agarose and the cheese regions (over a temperature range from 297K to 316K (FIG. 3C). A lipid proton saturation spectrum was obtained by applying the saturation pulse around the lipid proton resonance (approximately −3.5 ppm with respect to the water proton resonance). FIG. 3B shows that the extended T-WASSR spectra of both water PRF and lipid PRF exhibited consistent peak positions with $^1$H NMR spectra at each temperature. Both the T-WASSR spectra and the $^1$H NMR spectra show that the lipid PRF is insensitive to temperature changes, allowing a determination of absolute temperature using the lipid PRF as an internal reference. Similar to water PRF mapping, fitting the fat saturation spectral images pixel-by-pixel allows mapping the lipid PRF at high spatial resolution. In FIG. 3D, the water-lipid PRF difference maps were calculated at four temperatures using the measured water and lipid PRF maps at the same temperature. Quantitatively analyzed on a manually drawn ROI, the mean water-lipid PRF differences exhibited a clear linear dependence ($r^2$>0.999) on absolute temperature, i.e., $J\delta_{water-lipid}$=5.92 0.0082×T(K) or 3.67−0.0082×T(° C.). This result is close to that reported for ex vivo liver samples, where $J\delta_{water-lipid}$=3.83−0.0135×T (° C.). These results thus indicate it is possible to use the T-WASSR method to directly assess absolute temperature for tissues containing both water and fat with a validated calibration curve.

To test whether the acquisition speed of T-WASSR can be further increased, we also performed Lorentzian fitting on data sets with reduced points. The SNR of these in vitro measurements were estimated as 64 and 89 for ROI1 (agarose) and ROI2 (cheese) respectively. As can be seen in Table 1, fitting with a reduced number of points when the spectral resolution was reduced 3 times (i.e. from 25 Hz to 75 Hz) only produces ~4.1% relative deviation. The FWHM of ROI2 is almost twice that of ROI1, which allows reducing the number of data points by a factor of 3 without a significant impact on the result (relative deviation=1%). Using the criterion for the minimal spectral resolution found in the simulations, we expect to save at least half of the acquisition time for ROI2 by reducing the spectral resolution from 10 to 5 points per FWHM. For ROI1, conversely, the acceleration can be achieved through reducing the SW/FWHM, e.g. from 3.4 to 2, if only the temperature change within ROI1 is of interest.

Figure 4A:
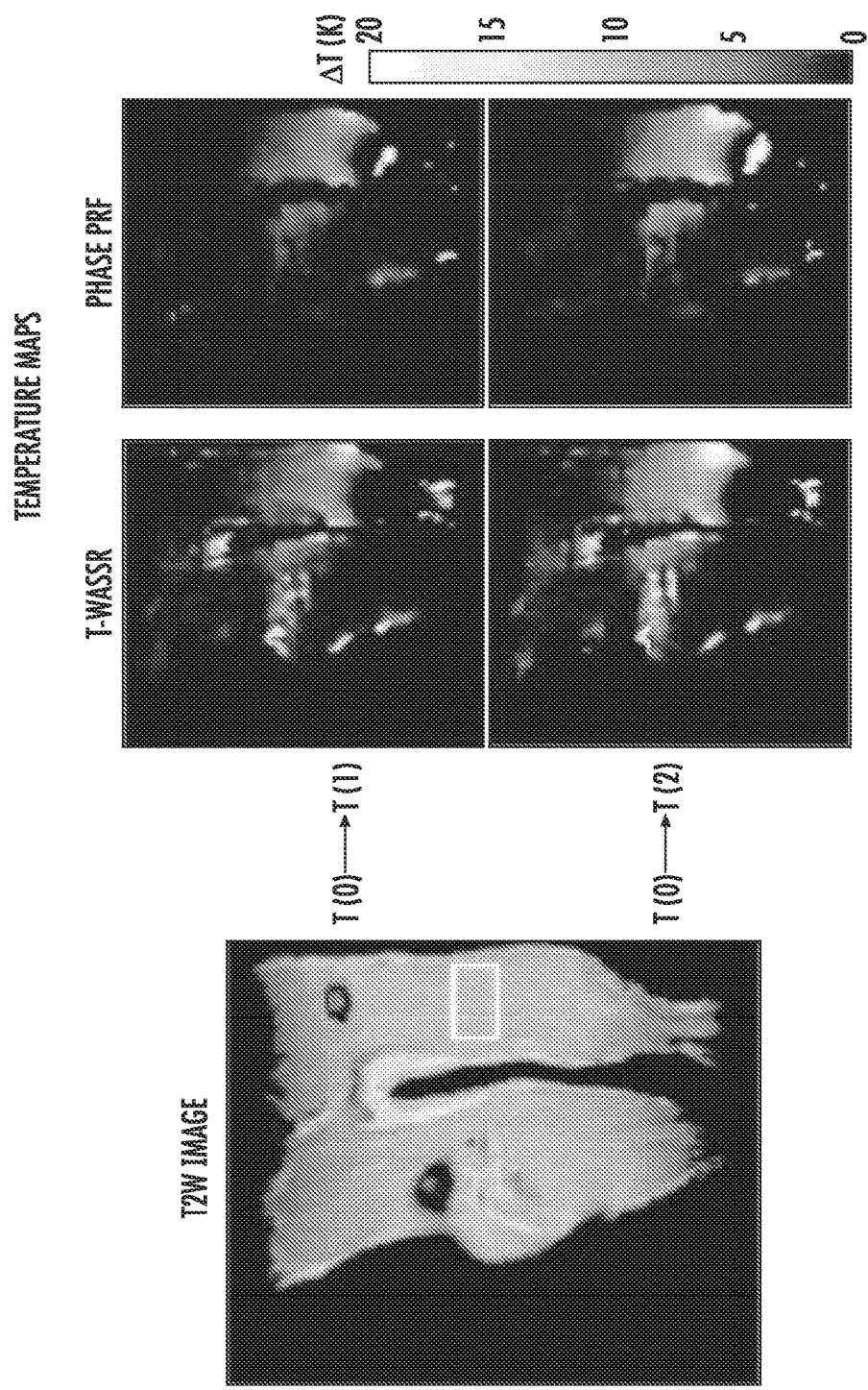
FIGS. 4A-4C illustrate in vivo temperature mapping of hyperthermia using the T-WASSR method.
Figure 4B:
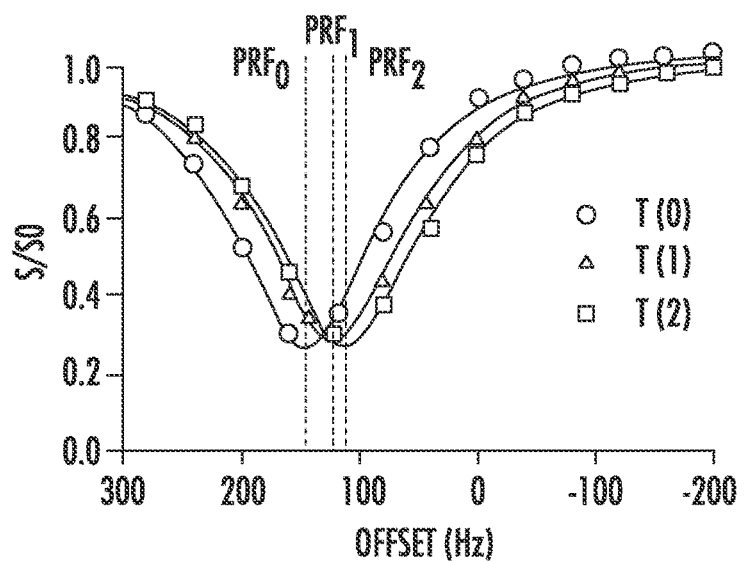
Figure 4C:
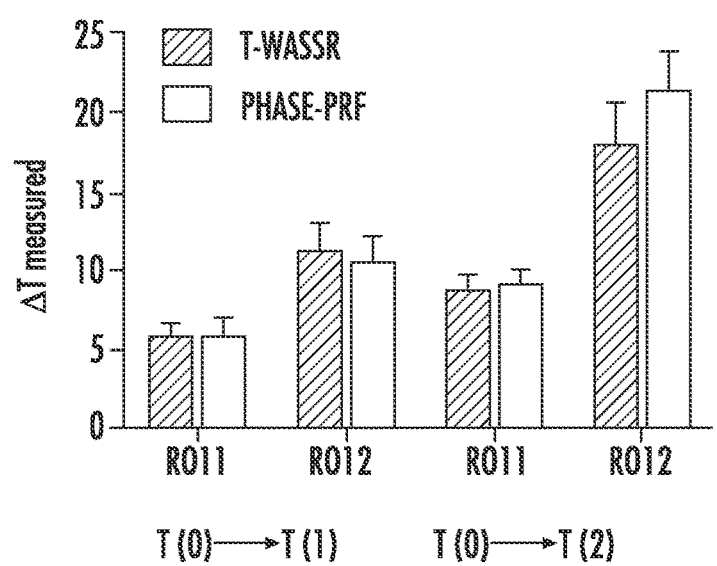

Finally, the feasibility of the in vivo application of the T-WASSR method was demonstrated in an animal model of local hyperthermia in the lower limbs at 9.4 Tesla. Due to the presence of a high $B_0$ inhomogeneity across the image (i.e., −500 Hz to +300 Hz as measured), we acquired T-WASSR spectra over a large frequency range (−800 to +800 Hz) at a spectral resolution of 40 Hz (approximately 4 points per FWHM). FIG. 4A shows that, for heating at T(1)=45° C. or T(2)=55° C., the ΔT maps obtained by TWASSR are consistent with those obtained by phase mapping, except for several regions that contained a noticeable amount of fat (appearing as high signal intensity regions on the RARE $T_{2w}$ image). As evident by the spectra of a selected ROI (ROI1) at different temperatures (FIG. 4B), the experimental spectral data could be well-fitted to a Lorentzian line shape for estimating water PRF shifts. As the temperature change was calculated by comparing the water PRF shift at each temperature during hyperthermia with that at T(0) (i.e., PRF1−PRF0 or PRF2−PRF0), the contibutions to water PRF shift by other temperature-independent factors, such as $B_0$ field inhomogeneity, were separated from that of temperature. The quantitative comparison was performed between the measured ΔT using T-WASSR and that of phase mapping for the same ROI as above and a secondary ROI corresponding to a small region close to the right knee, where a markedly high temperature increase was found (FIG. 4A). For the four groups of comparisons shown in FIG. 4C, the measured ΔTs were not statistically different (i.e., P<0.05, Student's t-test), except for ROI2 at T(2).

Similar to the in vitro study, we also listed the estimated water PRF shifts for both ROI1 and ROI2 at temperature T(0) using reduced data points in Table 2. The results show that, because the SNR of in vivo measurement is only moderate (<50) and the spectral resolution is approximately 4 points per FWHM (40 Hz), the ability to improve the temporal resolution through reducing data points is limited. However, it should be noted that the long acquisition time of the study was mainly a result of the use of very broad sweepwidth (1600 Hz) to compensate the large $B_0$ inhomogeneity. For example, for ROI1 where the FWHM is estimated as 157 Hz, the SW/FHWM is approximately equal to 10, which indicates that the acquisition time could be markedly shortened using a reduced sweepwidth for monitoring the temperature changes of a particular region.

A direct-saturation-based water approach for temperature mapping, adding additional methodology to the arsenal of non-invasive, high-resolution MRI thermometry is illustrated herein. The principles are based on the WASSR method, originally developed to determine $B_0$ inhomogeneities in the study of chemical exchange saturation transfer (CEST) imaging. Adapted to rapidly study the temperature-induced water PRF shift using Lorentzian fitting, the T-WASSR method demonstrated a good correlation with traditional phase PRF imaging and MR spectroscopy, both in vitro and in vivo. To implement the T-WASSR method with a minimal acquisition time without significantly comprising the measurement accuracy, technical guidelines based on the theoretical simulations are also provided. These technical guidelines have been verified in the current study and therefore can be used in the future studies.

The results demonstrated that the T-WASSR has an improved robustness of high-resolution temperature mapping in fat-containing tissues. As evident by our phantom study, the water DS spectrum is inherently separated from that of fat, eliminating the need for a priori knowledge of fat content and further data processing. The capability of measuring intra-voxel lipid PRF endows T-WASSR with additional advantages. First, monitoring the change of temperature-independent lipid PRF can be used to correct unwanted magnetic field drift when calculating temperatures. In the study, a drift of 6 Hz in lipid PRF after six hours was observed. More important, simultaneous measurement of both water and lipid PRF within the same imaging scheme (at a cost of double the acquisition time) enables high-resolution mapping of absolute temperature for tissues or regions containing both fat and water, if a pre-determined temperature-chemical shift difference calibration curve is available, as exemplified in FIG. 3D. These features make the T-WASSR method ideally suited for measuring temperatures in fat-containing tissues, such as the breast (29) and the liver (40).

Similar to the phase mapping method, the T-WASSR was shown capable of mapping temperature changes at high spatial resolution. It is, however, difficult to make a conclusive comparison of the temporal resolution between the two methods based on the studies, although the phantom study showed a comparable temporal and spatial resolution between the two methods. It is because the speed of a MRI method highly depends on many factors such as spatial resolution, number of averages, main field strength $B_0$, and hardware settings. However, T-WASSR appears to be slower than the phase mapping method due to the acquisition of multiple images. While the demonstrated temporal resolution, approximately two minutes for in vitro and eight minutes for in vivo imaging, may appear difficult for real-time temperature monitoring, the acquisition speed can be significantly enhanced. A fast spin echo RARE imaging sequence was used in the current study, which is not a time-efficient method, especially when the RARE factor was set to 8 for the in vivo studies. Because the proposed T-WASSR is implemented simply by adding saturation RF pulses in front of, in theory, any kind of imaging sequence, it is expected that the acquisition time can be further shortened using a faster imaging sequence. In addition to RARE, many fast sequences, including EPI, FLASH, FISP, and GRASE, have shown to be able to improve the temporal resolution of saturation transfer experiments. T-WASSR-based volumetric temperature mapping within a reasonable temporal resolution is also expected with the recent developments in 3D saturation transfer imaging.

For clinical translation of the T-WASSR method, the specific absorption rate (SAR) may be a limiting factor as a high number of saturation pulses within a short TR time results in a high duty cycle. However, the SAR may be effectively reduced by increasing TR times to increase the duty cycle and/or increase the number of k-space lines per saturation preparation.

Temperature-responsive water saturation shift referencing (TWASSR) can therefore be used to measure the change in water proton resonance frequency (PRF) in response to temperature changes. By fitting the water direct saturation spectrum to a Lorentzian line shape, the water PRF can be accurately determined, providing a means of noninvasively mapping temperature changes with high spatial resolution. As demonstrated both in vitro and in vivo, the proposed T-WASSR method provides results consistent with other MRI methods and is more robust for temperature measurements in fat-containing tissues.

The many features and advantages of the invention are apparent from the detailed specification, and thus, it is intended by the appended claims to cover all such features and advantages of the invention which fall within the true spirit and scope of the invention. Further, since numerous modifications and variations will readily occur to those skilled in the art, it is not desired to limit the invention to the exact construction and operation illustrated and described, and accordingly, all suitable modifications and equivalents may be resorted to, falling within the scope of the invention.

TABLE 1

The accuracy of Lorentzian fitting of the data sets truncated from the in vitro data using different spectral resolutions.

| Spectral resolution (Hz) | ROI1 | | | ROI2 | | |
|---|---|---|---|---|---|---|
| | Points/ FHWM | Estimated $B_0$ (Hz) | Relative deviation % | Points/ FHWM | Estimated $B_0$ (Hz) | Relative deviation % |
| 25 | 5.8 | −41.4 | | 9.8 | −58.9 | |
| 50 | 2.9 | −40.4 | 2.5 | 4.9 | −58.8 | 0.2 |
| 75 | 1.9 | −43.1 | 4.1 | 3.3 | −58.3 | 1.0 |
| 150 | 1.0 | −43.5 | 5.0 | 1.6 | −54.0 | 8.3 |

[a] FWHM for ROI1 and ROI2 were measured as 145 and 245 Hz respectively
[b] SNR for ROI1 and ROI2 were measured as 64 and 89 respectively
[c] Sweepwidth was 500 Hz for all the measurements (8250 Hz to +250 Hz)
[d] Relative deviation % was calculated as by $|(B_{0, Res} - B_{0.25 Hz})/B_{0.25 Hz}|$ %, where the $B_{0, Res}$ is the estimated $B_0$ at different spectral resolutions.

TABLE 2

The accuracy of Lorentzian fitting of the data sets truncated from the in vivo data using different spectral resolutions.

| Spectral resolution (Hz) | ROI1 | | | ROI2 | | |
|---|---|---|---|---|---|---|
| | Points/ FHWM | Estimated $B_0$ (Hz) | Relative deviation % | Points/ FHWM | Estimated $B_0$ (Hz) | Relative deviation % |
| 40 | 3.9 | 145.3 | | 4.3 | 313.3 | |
| 80 | 2.0 | 147.7 | 1.7 | 2.2 | 311.7 | 0.5 |
| 120 | 1.3 | 142.7 | 1.8 | 1.4 | 321.3 | 2.6 |
| 160 | 1.0 | 150.9 | 3.9 | 1.1 | 324.0 | 3.4 |

[a] FWHM for ROI1 and ROI2 was measured as 157 and 172 Hz respectively.
[b] SNR for ROI1 and ROI2 were measured as 42 and 39 respectively.
[c] Sweepwidth was 1600 Hz for all the measurements (8800 Hz to +800 Hz).
d Relative deviation % was calculated as by $|(B_{0, Res} - B_{0.40 Hz})/B_{0.40 Hz}|$ %, where the $B_{0, Res}$ is the estimated $B_0$ at different spectral resolutions.

What is claimed is:

1. A method for obtaining a magnetic resonance image spectrum of a subject comprising:
    performing a temperature-responsive water saturated shift referencing (T-WASSR) experiment of the subject at different temperatures regardless of tissue composition, and in particular regardless of fat content of the tissue using an MRI machine, wherein the T-WASSR experiment includes applying RF saturation pulses;
    measuring a chemical shift of water protons at the different temperatures;
    measuring a temperature-dependent water saturation spectrum;
    determining a temperature-dependent water peak in the presence of a lipid proton, wherein the temperature-dependent water peak is separated from that of the lipid proton;
    assessing a proton resonance frequency of water (water PRF);
    measuring a change in the water PRF in response to temperature changes;
    assessing saturation spectrum for the fat content of the tissue at the different temperatures;
    estimating proton resonance frequency for the fat content of the tissue at the different temperatures; and,
    detecting and creating a map of temperature changes for the subject and displaying the map of those temperature changes.

2. The method of claim 1 further comprising creating an image of at least a portion of the subject using the water PRF.

3. The method of claim 2 wherein the image depicts temperature and temperature-induced shifts.

4. The method of claim 1 further comprising mapping the temperature of fat containing tissue.

5. The method of claim 1 further comprising measuring fat resonance frequency.

6. The method of claim 5 further comprising using the fat resonance frequency to provide an internal reference to account for the field shift caused by non-temperature related factors.

7. The method of claim 5 further comprising measuring absolute temperature of the fat containing tissue.

8. The method of claim 1 further comprising determining a maximum of frequency for water direct saturation spectrum at various temperatures.

9. The method of claim 8 further comprising using a Lorentzian line shape.

10. The method of claim 1 further comprising calculating a change in temperature using the difference in water PRF shifts.

11. A system for obtaining a magnetic resonance image spectrum of a subject comprising:
    a magnetic resonance imaging (MRI) machine configured to obtain the magnetic resonance image spectrum of the subject including applying saturation pulses;
    a non-transitory computer readable medium programmed to:
    perform a temperature-responsive water saturated shift referencing (T-WASSR) experiment of the subject at different temperatures regardless of tissue composition, and in particular regardless of fat content of the tissue;
    measure a chemical shift of water protons at the different temperatures;
    measuring a temperature-dependent water saturation spectrum;
    determine a temperature-dependent water peak in the presence of a lipid proton, wherein the temperature-dependent water peak is separated from that of the lipid proton;
    assess a proton resonance frequency of water (water PRF);
    measure a change in the water PRF in response to temperature changes;
    assess saturation spectrum for the fat content of the tissue at the different temperatures;
    estimate resonance frequency for the fat content of the tissue at the different temperatures; and,
    detect and create a map of temperature changes for the subject and display the map of those temperature changes.

12. The system of claim 11 further comprising the non-transitory computer readable medium being programmed to create an image of at least a portion of the subject using the water PRF.

13. The system of claim 12 wherein the image depicts temperature and temperature-induced shifts.

14. The system of claim 11 further comprising the non-transitory computer readable medium being programmed to map the temperature of fat containing tissue.

15. The system of claim 11 further comprising the non-transitory computer readable medium being programmed to measure fat resonance frequency.

16. The system of claim 15 further comprising the non-transitory computer readable medium being programmed to use the fat resonance frequency to provide an internal reference to account for the field shift caused by non-temperature related factors.

17. The system of claim 15 further comprising the non-transitory computer readable medium being programmed to measure absolute temperature of the fat containing tissue.

18. The system of claim 11 further comprising the non-transitory computer readable medium being programmed to determine a maximum of frequency for water direct saturation spectrum at various temperatures.

19. The system of claim 18 further comprising the non-transitory computer readable medium being programmed to use a Lorentzian line shape.

20. The system of claim 11 further comprising the non-transitory computer readable medium being programmed to calculate a change in temperature using the difference in water PRF shifts.

* * * * *